(12) United States Patent
Coute et al.

(10) Patent No.: US 7,498,475 B2
(45) Date of Patent: Mar. 3, 2009

(54) MOLECULAR SIEVE MIXTURES FOR OLEFIN FORMATION

(75) Inventors: Nicolas P. Coute, Houston, TX (US); Machteld M. Mertens, Boortmeerbeek (BE); Marcel J. Janssen, Kessel-Lo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 723 days.

(21) Appl. No.: 11/122,450

(22) Filed: May 5, 2005

(65) Prior Publication Data

US 2006/0195001 A1 Aug. 31, 2006

Related U.S. Application Data

(60) Provisional application No. 60/656,595, filed on Feb. 25, 2005.

(51) Int. Cl.
*C07C 1/00* (2006.01)
*B01J 27/182* (2006.01)

(52) U.S. Cl. .................... 585/640; 585/639; 502/214

(58) Field of Classification Search ......... 585/638–640; 502/67, 214

See application file for complete search history.

(56) References Cited

U.S. PATENT DOCUMENTS

| 5,972,203 | A | 10/1999 | Smith et al. | 208/113 |
| 6,486,219 | B1 * | 11/2002 | Janda et al. | 518/706 |
| 2002/0165089 | A1 * | 11/2002 | Janssen et al. | 502/214 |
| 2002/0165090 | A1 | 11/2002 | Janssen et al. | 502/214 |
| 2003/0004384 | A1 | 1/2003 | Coute et al. | 585/639 |
| 2006/0106270 | A1 * | 5/2006 | Glover et al. | 585/639 |

FOREIGN PATENT DOCUMENTS

| WO | WO 03/000411 | 1/2003 |
| WO | WO 2004/060559 | 7/2004 |

* cited by examiner

*Primary Examiner*—In Suk Bullock

(57) ABSTRACT

Molecular sieve catalysts are combined to provide a catalyst mixture having a beneficial combination of the activities and selectivities of the individual molecular sieves. The molecular sieve catalysts can be formulated or unformulated silicoaluminophosphate molecular sieves, silicoaluminate molecular sieves, and/or metalloaluminophosphate molecular sieves.

11 Claims, 2 Drawing Sheets

MOLECULAR SIEVE MIXTURES FOR OLEFIN FORMATION

CROSS REFERENCE TO RELATED APPLICATIONS

This application claims the benefit of Provisional Application No. 60/656,595 filed Feb. 25, 2005, the disclosure of which is fully incorporated herein by reference.

FIELD OF THE INVENTION

This invention relates to physical mixtures of molecular sieves, including their formulation and use for converting hydrocarbons to olefins. In particular, this invention relates to mixtures of molecular sieves for use as catalysts in converting oxygenates such as methanol to olefins.

BACKGROUND OF THE INVENTION

Conventional production processes for converting petroleum feedstock into olefins typically involve molecular sieve catalysts. Molecular sieve catalysts generally contain molecular sieve particles that act as the catalyst component. An example of a molecular sieve that acts as a catalyst in converting oxygenates to olefins is a silicoaluminophosphate (SAPO) molecular sieve. Such molecular sieves contain a pore system, which is a network of uniform pores and empty cavities. These pores and cavities catch molecules that have a size equal to or less than the size of the pores and cavities, and repel molecules of a larger size. The active sites of the molecular sieves that have catalytic activity are generally located within the pores and cavities such that feed enters into the pores, contacts the active catalytic site, and is converted to product.

Molecular sieve catalysts can be characterized in terms of their activity and selectivity. The activity of a molecular sieve catalyst refers to the reaction rate for conversion of methanol (or another oxygenate) to olefin in the presence of the catalyst. The selectivity of molecular sieve catalyst refers to the type of olefins produced during the conversion reaction. For example, the prime olefin selectivity of a catalyst refers to the amount of ethylene and propylene produced relative to the total amount of olefin produced during a reaction.

One of the challenges in using molecular sieve catalysts is balancing the reactivity of the molecular sieve against the selectivity of the molecular sieve for producing desired olefins. Using conventional catalysts, it is possible to select a catalyst that provides the highest reaction rate for a given set of reaction conditions. A higher reaction rate can allow more feedstock to be processed in a reactor of fixed volume, or can reduce the required size of reactor needed to process a quantity of feedstock. However, catalysts with higher reaction rates typically also have lower selectivities for production of ethylene and propylene. Although more of the initial oxygenate feedstock is converted to a product, the percentage that is converted to the desired light olefin products is reduced. Catalysts with higher reactions rates also often produce increased amounts of coke. Coke is a carbon by-product of a conversion reaction that tends to deposit on the surface of the catalyst, leading to decreases in catalyst reactivity.

U.S. Patent Application Publication 2002/0165090 describes the preparation of SAPO molecular sieve catalysts that have intergrown phases. These intergrowth materials are composed of molecular sieve crystals that contain two separate frameworks, such as AEI and CHA.

U.S. Patent Application Publication 2003/0004384 describes a method for converting oxygenates to olefins. Either individual molecular sieves combined into one catalyst particle or mixtures of catalytic particles each containing a single molecular sieve can be used in the conversion reaction. Specifically described are two types of catalyst mixtures: one where each catalyst particles contains more than one type of SAPO molecular sieve, and one where each particle contains only one type of SAPO molecular sieve, but more than one type of SAPO molecular sieve catalyst particle is present.

What is needed is a catalyst or catalyst formulation that allows for improved conversion of an initial feedstock while minimizing the loss of reaction selectivity in producing desired olefins. The catalyst or catalyst formulation should be compatible with existing reaction systems.

SUMMARY OF THE INVENTION

In a first embodiment, the invention provides a catalyst having a physical mixture of: a molecular sieve having an activity $K_A$, a prime olefin selectivity $S_A$, and a weight fraction x relative to a total weight of molecular sieve in the physical mixture; and a second molecular sieve having an activity $K_B$, a prime olefin selectivity $S_B$, and a weight fraction (1−x) relative to the total weight of molecular sieve in the physical mixture, wherein $K_A/K_B$ is at least 1.5, and $S_A/S_B$ is less than 1. Preferably, the molecular sieves are selected from the group consisting of silicoaluminophosphate molecular sieves, silicoaluminate molecular sieves, and metalloaluminophosphate molecular sieves.

In another embodiment, the activities of the molecular seives further satisfy the relation $K_{mix} > 0.9*[x*K_A+(1-x)*K_B]$. In still another embodiment, the selectivities of the molecular sieves satisfy the relation $S_{mix} = \beta*x*S_A + (1-\beta*x)*S_B$, where $\beta$ has a value of less than 1, such as 0.75, 0.5, 0.33, or 0.25. In still another embodiment, the molecular sieves further have coke selectivities $C_A$ and $C_B$ that satisfy the relation $C_{mix} < x*C_A+(1-x)*C_B$. Yet further embodiments include any one or more of the above embodiments in combination with the first embodiment.

The invention also provides a method for performing an oxygenate to olefin conversion reaction using a mixture of molecular sieves as described above.

DETAILED DESCRIPTION OF THE INVENTION

I. Overview

Figure 1:
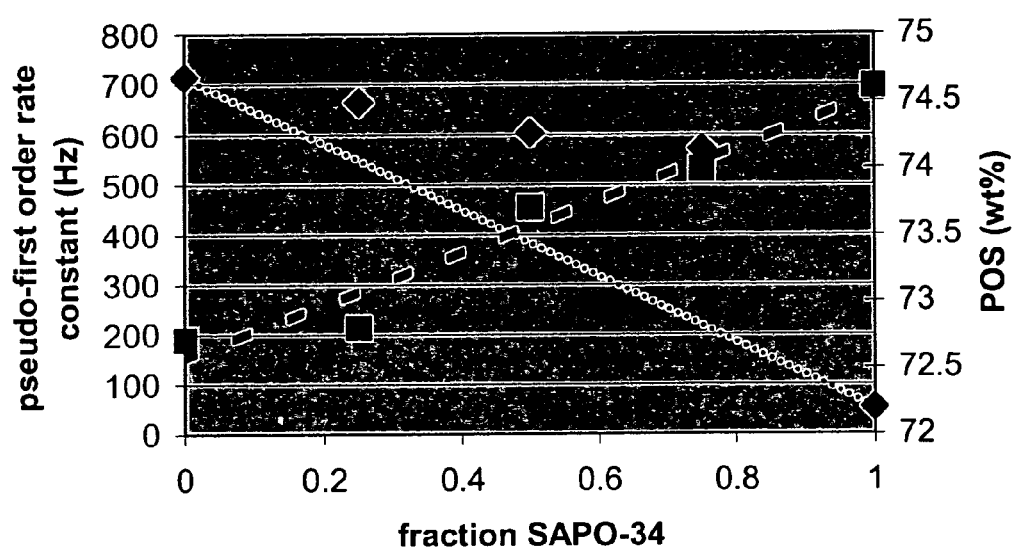
FIG. 1 depicts the activity and selectivity for a series of catalyst mixtures according to an embodiment the invention.

This invention is directed to physical mixtures of molecular sieves for use in oxygenate to olefin conversion reactions. The molecular sieves comprising the mixture are selected so that one of the sieves exhibits a higher selectivity for producing a desired product, while the second shows a higher reactivity. The resulting catalyst mixture will have a selectivity similar to the higher selectivity of the first molecular sieve, while having a reactivity that is roughly an average of the reactivities for the two molecular sieves. In various embodiments of this invention the catalyst mixtures refer to mixtures of catalyst particles. The particles themselves can contain one or more than one type of molecular sieve component, as long as the overall mixture contains at least two types of molecular sieve components. In particular, the catalyst mixtures of this invention provides an advantage when molecular sieves with sharply differing activities and selectivities are combined. It would be expected that the preferred way to develop a high selectivity catalyst mixture would be to combine two separate molecular sieves that each have a high selectivity. According to the invention, however, one high selectivity molecular sieve is sufficient to produce a catalyst mixture with high selectivity. This allows the second molecular sieve in the mixture to be selected to provide a more reactive catalyst that will improve the reaction rate for the conversion reaction.

The selectivity $S_x$ of a catalyst refers to the amount of a given product produced relative to the amount of feedstock converted. Thus, a catalyst with a higher selectivity for production of ethylene will produce a higher percentage of ethylene during a conversion reaction. In various embodiments of the invention, one of the molecular sieves in the catalyst mixture should be selected to have a high selectivity. The selectivity $S_{mix}$ of a catalyst mixture will be similar to the selectivity of the molecular sieve with the highest selectivity. Other molecular sieves in the mixture will cause only a modest reduction in selectivity.

The reactivity of a molecular sieve catalyst or catalyst containing a mixture of molecular sieves can be expressed as an activity $K_X$, where the subscript X denotes the particular catalyst or catalyst mixture. (For example, the activities of two molecular sieves in a mixture may be referred to as $K_A$ and $K_B$). The activity $K_x$ is a reaction rate constant, so higher activity values correspond to faster reaction rates for a conversion reaction. Conventional catalysts with a high selectivity typically have a relatively low reactivity. Therefore, in various embodiments of the invention, the second molecular sieve in the catalyst mixture should be selected to have a high reactivity in order to raise the overall reactivity of the reaction mixture.

By combining a high selectivity molecular sieve with a high activity molecular sieve, a catalyst mixture can be created that maintains a desired selectivity while providing a higher reaction rate than is available using a conventional catalyst. From a practical standpoint, the mixtures of this invention allow for faster conversion of oxygenate feedstock with only a minimal reduction in the percentage of desired products. This advantage can be used to process more feedstock in a reactor of constant size, or to process a fixed amount of feedstock in a reactor of reduced size.

In various embodiments, the mixtures of this invention also reduce the production of coke on catalyst particles. The molecular sieve catalysts are selected so that one of the molecular sieves exhibits a higher reactivity, while the second has a lower coke selectivity (i.e., produces a lower percentage of coke). During a conversion reaction, the mixture provides the benefit of the higher reaction rate of the first molecular sieve with only a small increase in the percentage of coke produced.

In an embodiment, the invention provides a physical mixture of catalyst particles that contains x of a first molecular sieve (A) and (1−x) of a second molecular sieve (B), where x has a value of between 0 and 1. In order to achieve the benefits of combining a high selectivity molecular sieve and high reactivity molecular sieve as described above, the individual molecular sieves in the catalyst mixture are selected to satisfy two or more of the following conditions:

1) The molecular sieves A and B have activities $K_A$ and $K_B$ respectively, with the ratio of activities $K_A/K_B$ being 1.5 or greater, or 2.5 or greater, or 3.5 or greater.

2) The molecular sieves A and B have selectivities for producing a desired product of $S_A$ and $S_B$ respectively, with the ratio of selectivities $S_A/S_B$ being less than 1.

3) The activity $K_{mix}$ of the physical mixture satisfies the relation $K_{mix} > 0.9*[x*K_A+(1-x)*K_B]$.

4) The selectivity $S_{mix}$ of the physical mixture satisfies the relation $S_{mix}=\beta*x*S_A+(1-*x)*S_B$, where $\beta$ is 0.75 or less, or 0.5 or less, or 0.33 or less, or 0.25 or less.

Conditions 1 and 2 relate to the properties of the individual molecular sieves included in the mixture. In an embodiment, molecular sieve A has a higher activity than molecular sieve B, while molecular sieve B has a higher selectivity than molecular sieve A. The higher "activity" of molecular sieve A refers to a pseudo-first order rate constant calculated at the maximum conversion of methanol to olefin in the presence of molecular sieve A. In an embodiment, the pseudo-first order rate constant corresponding to the activity of molecular sieve A is at least 1.5 times greater than the pseudo-first order rate constant for molecular sieve B calculated under the same or similar conditions. In other embodiments, the activity of molecular sieve A can be at least 2.5 times greater than the activity of molecular sieve B, or at least 3.5 times greater than the activity of molecular sieve B. The higher "selectivity" of molecular sieve B refers to the percentage production of a desired product relative to the amount of feedstock reacted in a methanol-to-olefin reaction. In various embodiments, the selectivity can refer to the percentage of ethylene produced (ethylene selectivity), the percentage of propylene produced (propylene selectivity), or the percentage of combined ethylene and propylene (prime olefin selectivity).

Condition 3 relates to a comparison between the activity of the molecular sieves in the catalyst mixture and the activities of the individual molecular sieves. Due to experimental errors and other small variations, the measured pseudo-first order rate constant for the catalyst mixture may be lower or higher than a weighted average of the pseudo-first order rate constants of the individual molecular sieves. In an embodiment, Condition 3 accounts for the potential variation in pseudo-first order rate constants by requiring the activity of the catalyst mixture to be at least 90% of a weighted average of the activities of the individual molecular sieves. In an alternative embodiment, the potential variation in pseudo-first order rate constants is accounted for by requiring the activity of the catalyst mixture to be at least 80% of a weight average of the activities of the individual molecular sieves. In still another embodiment, the activity of the catalyst mixture roughly corresponds to a weighted average of the activities of the individual molecular sieves.

Condition 4 relates to the selectivity of the catalyst mixture. In an embodiment, the selectivity of the catalyst mixture does not directly vary according to a weighted average of the selectivities of the individual molecular sieves. Instead, the selectivity of the catalyst mixture is higher than the value predicted by a weighted average. This is represented in condition 4 by the scaling factor $\beta$. Scaling factor $\beta$ reduces the "apparent amount" of molecular sieves A present in the physical mixture. Thus, instead of using the actual weight percent of molecular sieves A (x) and molecular sieves B (1−x) in the physical mixture, condition 4 uses the apparent amount of molecular sieves A ($\beta$x) and molecular sieves B (1−$\beta$x) present in the mixture.

In an embodiment, the physical mixture of catalysts produces less coke than would be expected based on a weighted average of the coke selectivities of the individual catalysts. In other words, the coke selectivity $C_{mix}$ of the catalyst mixture satisfies the relation $$C_{mix} < x*C_A + (1-x)*C_B$$

where $C_A$ and $C_B$ are coke selectivities of the individual molecular sieves in the catalyst mixture.

In yet another embodiment, the physical mixture of molecular sieves comprises two or more molecular sieves in one catalyst particle. In such an embodiment, the activity of the physical mixture roughly corresponds to the weighted average of the activities of the two or more molecular sieves. Additionally, the selectivity of the physical mixture is greater than the value predicted by a simple weighted average of the selectivities of the individual molecular sieves.

The physical mixture of molecular sieves can be used in various forms. In one embodiment, the physical mixture of molecular sieves is a mixture of two or more different molecular sieves without formulation. In another embodiment, the physical mixture comprises two or more molecular sieves that are formulated individually into catalyst particles. These formulated molecular sieve catalyst particles, which each contain only one type of molecular sieve, can then be mixed together to provide a mixture of catalyst particles containing the two types of molecular sieves. In still another embodiment, the physical mixture comprises two or more molecular sieves that are formulated together into formulated catalyst particles. In this embodiment, the two or more molecular sieves may both be present within a single formulated catalyst particle. In various embodiments, the physical mixture of molecular sieves can be composed of any two or more molecular sieves having the desired characteristics. Preferred molecular sieves are selected from the group consisting of silicoaluminophosphate molecular sieves, metalloaluminophosphate molecular sieves, and silicoaluminate molecular sieves.

In an embodiment, the weight of each molecular sieve in the mixture represents roughly half of the total weight of molecular sieve in the catalyst mixture. In other words, each molecular sieve comprises roughly 50% by weight of the total weight of molecular sieve in the catalyst mixture. In another embodiment, each molecular sieve comprises at least 5% by weight of the total weight of molecular sieve in the catalyst mixture. In still other embodiments, each molecular sieve comprises at least 10% by weight, or at least 15% by weight, or at least 20% by weight, or at least 25% by weight, or at least 30% by weight of the total weight of molecular sieve in the catalyst mixture.

In an embodiment, the high activity catalyst is a SAPO-34 molecular sieve. In another embodiment, the high selectivity catalyst is a molecular sieve that is an intergrowth material comprising silicoaluminiophosphate molecular sieve.

In various embodiments, the catalyst mixtures of this invention are suitable for use in reaction systems for converting oxygenate feedstocks (or other hydrocarbon feedstocks) to olefins. The conversion reaction is performed by contacting a catalyst mixture according to an embodiment of the invention with an oxygenate feedstock within the reaction system.

II. Use of Weighted Averages for Expressing Properties of Catalyst Mixtures

One convenient method for describing and/or predicting the properties of the physical mixtures of catalyst particles provided by this invention is in comparison to the properties of the individual molecular sieves. For example, the properties of the physical mixture can be expressed in relation to a weighted average of the properties of the individual molecular sieves. In a mixture containing two types of molecular sieves (A and B), the fraction by weight of the molecular sieves corresponding to molecular sieve A can be designated as "x". The remaining molecular sieve in the mixture corresponds to molecular sieve B, and this weight fraction can be expressed as "1−x". Therefore, for a property P of the catalyst mixture, a predicted value of the property P for a mixture of molecular sieves can be calculated using the formula:

$$x*P_A + (1-x)*P_B = P_{mix} \qquad (1)$$

It has been discovered that the properties of a molecular sieve or catalyst mixture can differ significantly from the values predicted by a simple weighted average. For example, for a given property of the mixture, one of the molecular sieves may not have a strong impact on the behavior of the mixture. In other words, one of the molecular sieves can have proportionally less influence on the mixture than would be indicated by the amount present. This concept can be incorporated into a weighted average using the formula $$\beta*x*P_A + (1-\beta*x)*P_B = P_{mix} \qquad (2)$$

where $\beta$ is a number between 0 and 1. In this formula for describing and/or predicting the value of a property P for the mixture of molecular sieves, the apparent amount of molecular sieve A in the mixture is not "x", but instead is the smaller "$\beta*x$". Similarly, the apparent amount of molecular sieves B in the mixture is the larger "$1-\beta*x$."

Note that the apparent amount of molecular sieves A and B in the mixture may be different for each property P. In other words, each property P can have a different value of $\beta$ associated with it in formula 2. As an example, in an embodiment the activity of a catalyst mixture can indicate that the apparent amount of molecular sieves A and B in the mixture roughly corresponds to the actual amount. In terms of formula 2, when the property P is activity, the value of $\beta$ is close to or equal to 1. In the same embodiment, the selectivity of the mixture can indicate an apparent amount of molecular sieve A that is lower than the actual amount. In terms of formula 2, the value of $\beta$ associated with the selectivity is not the same as the value of $\beta$ for the activity. Instead, the value of $\beta$ associated with the selectivity is less than 1, such as 0.75, 0.5, 0.33, or 0.25.

III. Determining Catalyst Properties

A. General Experimental Details

The properties of the molecular sieves and molecular sieve mixtures described in this invention were determined by performing a methanol-to-olefin conversion reaction in a fixed bed reactor equipped with an online gas chromatograph (GC) and a 16 port sampling valve. The 16 port sampling valve was used to capture samples of the products of the methanol-to-olefin conversion reaction. The samples were acquired consecutively during the course of the reaction, and continued until all 16 sampling ports were used, at which point the conversion reaction was stopped.

B. Determining Catalyst Activity

In various embodiments of this invention, the activity of a molecular sieve or molecular sieve mixture refers to a calculated pseudo-first order rate constant for conversion of methanol to olefins by the molecular sieve or molecular sieve mixture. The pseudo-first order rate constant is calculated based on a measured value for the maximum methanol conversion rate for the molecular sieve or molecular sieve mixture. To determine the maximum methanol conversion rate, the molecular sieve or molecular sieve mixture is placed in a fixed bed reactor as described above. The molecular sieve is then used to perform a methanol-to-olefin conversion under conditions where the maximum methanol conversion rate is less than 80%. Due to the buildup of coke during the conversion reaction, the conversion rate is not constant. The maximum methanol conversion rate refers to the sample (out of the 16 possible samples) that shows the highest rate of methanol conversion.

Based on the measured maximum methanol conversion rate, a pseudo-first order rate constant can be calculated using the formula $$K = -[\ln((100-Y)/100)]/t \qquad (3)$$

where

K is the pseudo-first order rate constant (1/sec);

Y is the maximum methanol conversion (%); and t is residence or space time (sec).

In an embodiment, the activity (pseudo-first order rate constant) of one or more of the molecular sieves is at least 100/sec, or at least 200/sec, or at least 300/sec, or at least 400/sec, or at least 500/sec, or at least 600/sec, or at least 700/sec, or at least 800/sec.

C. Determining Prime Olefin Selectivity of Catalysts

In an embodiment, the selectivity of a molecular sieve or molecular sieve mixture refers to prime olefin selectivity (POS). The prime olefin selectivity represents the weight percent of ethylene and propylene produced versus the total weight of all products formed during a conversion reaction for converting methanol to olefins. The additional products produced by the conversion reaction include heavier olefins as well as coke. In alternative embodiments, the selectivity can refer to the selectivity for producing ethylene or the selectivity for producing propylene. For example, SAPO-18 is a molecular sieve that selectively produces more propylene than ethylene.

To determine the selectivity for producing an individual product, the POS for a molecular sieve or molecular sieve mixture, or another measure of selectivity, a molecular sieve or molecular sieve mixture is placed in a fixed bed reactor equipped with an on line-GC and a 16 port sampling valve as described above. The molecular sieve or molecular sieve mixture is then used to perform a methanol-to-olefin conversion under condition similar to the conditions used for determining the maximum methanol conversion rate.

The 16 samples are analyzed to determine the resulting products of the conversion reaction. Coke formation can, in addition to changing the rate constants, also influence the products produced during the conversion reaction. As a result, the selectivity for production of a given product for a molecular sieve or molecular sieve mixture is determined by calculating an average selectivity over the entire course of the experiment.

Average selectivities are calculated based on the formula, $$[(x_1)(s_1) + (x_2-x_1)(s_1+s_2)/2 + (x_3-x_2)(s_2+s_3)/2 + (x_4-x_3)(s_3+s_4)/2 + \ldots]/CMCPS,$$

where $s_i$ is the weight percent of a product in a particular sample of the conversion reaction output (such as ethylene, propylene, etc.), $x_i$ is the amount (grams) of methanol converted per gram of molecular sieve, and CMCPS is the cumulative amount of methanol converted.

In an embodiment where the selectivity is prime olefin selectivity, the POS of one or more of the molecular sieves is at least 50%, or at least 60%, or at least 65%, or at least 70%, or at least 72.5%, or at least 75%, or at least 80%.

D. Determining Coke Selectivity of Catalysts

In various embodiments of the invention, the coke selectivity of a molecular sieve or molecular sieve mixture refers to the weight percent of coke produced as a product during a methanol to olefin conversion reaction. The coke selectivity was calculated based on the difference between C/H ratio of the feed and the C/H ratio of the total effluent product, obtained during the same experiment where the prime olefin selectivity was determined. In an embodiment, the coke selectivity of one or more of the molecular sieves is 5% or less, or 4% or less, or 3% or less, or 2% or less.

IV. Types of Catalyst Mixtures

In various embodiments, the catalyst mixtures of this invention are composed of silicoaluminophosphate, silicoaluminate and metalloaluminophosphate molecular sieves. Examples include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON and intergrowth materials incorporating these molecular sieves. In one preferred embodiment, one of the molecular sieves of the invention has an AEI topology or a CHA topology, most preferably a CHA topology. In another embodiment, one of the molecular sieves is an intergrowth material of AEI and CHA.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second. Completely Revised and Expanded Edition, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12- ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871

(SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, at least one of the molecular sieves, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or an intergrowth of SAPO-34 and SAPO-18, and metal containing molecular sieves thereof.

In another embodiment, one or more molecular sieves can be an intergrowth material having two or more distinct phases of crystalline structures within one molecular sieve composition. Examples of intergrowth molecular sieves useful in this invention include those described in U.S. Patent Application Publication No. 2002-0165089 and International Publication No. WO 98/15496, published Apr. 16, 1998, the descriptions of those sieves incorporated herein by reference. Note that SAPO-18, AlPO-18 and RUW-18 have an AEI framework-type, and SAPO-34 has a CHA framework-type, and that preferred molecular sieves used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

The molecular sieves of this invention can be either formulated or unformulated. When formulated, the formulated molecular sieve catalyst particles can be of any conventional shape or size, including, but not limited to, those catalyst types made by spray drying, pelletizing, extrusion, and any of various conventional sphere-making techniques. In an embodiment, each type of molecular sieve can be incorporated into each formulated catalyst particle. In another embodiment, each formulated catalyst particle contains only one type of molecular sieve, or some number of molecular sieves that is less than the total number of molecular sieves present in the mixture. In still another embodiment, the formulated molecular sieve catalyst particles can be admixed with other particles that do not contain any molecular sieve.

Formulated molecular sieve catalyst particles are made or formulated by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieves, in a preferred embodiment, are combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

Inert solid particles can be flowed through the reactor system of this invention. The inert solid particles can be mixed with solid catalyst particles or used as carrier materials for any conventional catalyst. Examples of such inert solid materials include oxides, such as silica, alumina, titania and zirconia. Of these oxides, silica is preferred. Silica is inherently inert, differing from other solid materials, and can serve as an excellent binder for the ingredients of the oxide catalyst composition without impairing the selectivity of many catalyst compositions. Such material also serves to impart the resulting catalyst composition with a high attrition resistance. When used as carrier, the silica can be in the range of about 30% to about 70% by weight, preferably about 40% to about 60% by weight, based on the total weight of the catalyst composition and the carrier.

V. Detailed Description of Preferred Reaction Systems

In a preferred embodiment of the invention, the reaction system is a system for converting oxygenates to olefins or a catalytic cracking reaction system. More preferably, the reaction system is a system for converting oxygenates to olefins or an olefin forming reaction system. The reaction system preferably includes both a reactor and a regenerator.

In one embodiment of the invention, the reaction system is an olefin forming reaction system in which feedstock is converted into one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or, alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contain one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent (s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds,* Grace, Avidan and Knowlton, eds., Blackie, 1997 (336-337).

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

In an alternative embodiment that can be optionally combined with the processes described above, the olefin(s) produced are directed to one or more polymerization processes for producing various polyolefins. Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the polymerization process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

VI. Example of Measurements of Activity and Selectivity

In a working embodiment, two molecular sieves were combined to form a physical mixture according to the invention. One molecular sieve was a SAPO-34 type molecular sieve with a Si:Al ratio of roughly 0.16. This SAPO-34 type molecular sieve was formed by mixing Condea Pural SB, 85% phosphoric acid in water (DPA), Ludox AS40, and 35% tetraethylammoniumhydroxide (TEAOH) in water. The relative amounts of the components were selected to produce a mixture with the composition

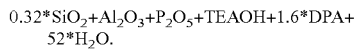

This mixture was heated to 170° C. over a 12 hour period and maintained at 170° C. for another 60 hours while stirring. After cooling, the synthesis slurry was washed and the solid was recovered by drying at 120° C.

The second molecular sieve was an AEI/CHA intergrowth material having a Si:Al ratio of roughly 0.06. This molecular sieve was formed by mixing 85% phosphoric acid in water with Ludox AS40. This mixture was homogenized and then cooled to 15° C. 35% TEAOH in water was added and again mixed until homogenous. Condea Pural SB was then added and mixed until homogenous. The relative amounts of the components were selected to produce a mixture with the composition

The synthesis mixture was then heated to 175° C. over a 12.5 hour period and maintained at 175° C. for another 50 hours while stirring. After cooling, the synthesis slurry was washed and the solid was removed by drying at 120° C.

After synthesis, the SAPO-34 and the intergrowth molecular sieves were used individually and as physical mixtures in reactions for converting methanol to light olefins. The weight ratios of molecular sieves investigated were 1:0; 0.75:0.25; 0.5:0.5; 0.25:0.75; and 0:1. The activity and selectivity of for conversion of methanol to olefins was measured for each molecular sieve or molecular sieve mixture.

To measure the catalytic activity, the molecular sieve (or molecular sieve mixture) was placed in a fixed bed reactor configured for a methanol-to-olefin reaction and equipped with an on-line gas chromatograph. The methanol-to-olefin reaction was carried out at 455° C. The methanol feedstock flow had a weight-hourly-space-velocity of between 600/hr and 1300/hr and a methanol pressure of 44 psia. The reaction conditions were selected to produce a maximum methanol conversion rate Y of less than 80%. The maximum conversion rates and the time required to obtain maximum conversion were measured and used to calculate a pseudo-first order rate constant K based on the formula $$K=-[\ln((100-Y)/100)]/t \qquad (3)$$

where

K is the pseudo-first order rate constant (1/sec);

Y is the maximum methanol conversion (%); and t is residence or space time (sec).

The prime olefin selectivity was measured in a separate experiment conducted at 475° C. and at a weight-hour-space-velocity of 100/hr. The products of the converted methanol were measured and the prime olefin selectivity was calculated based on the weight of ethylene and propylene produced relative to the total weight of converted products. The coke selectivity was also calculated.

FIG. 1 shows a plot of the calculated activity and selectivity for the individual molecular sieves and the molecular sieve mixtures. The bottom axis of the graph indicates the proportion of the SAPO-34 type molecular sieve used for the conversion reaction, with "0" indicating a reaction using only the intergrowth composition and "1" indicating a reaction using only the SAPO-34 type molecular sieve. FIG. 1 shows that the individual molecular sieve have distinct properties. The pseudo-first order rate constant from the SAPO-34 type molecular sieve (about 700/sec) is roughly 3.5 times as great as the rate constant for the intergrowth material (about 200/sec). On the other hand, the prime olefin selectivity of the intergrowth material (about 74.5%) is greater than the selectivity of the SAPO-34 type molecular sieve (about 72%).

The lines in FIG. 1 represent predictions based on simple weighted averages of the properties of the molecular sieves while the data points show the measured values of the activity and selectivity. For the activity, the measured pseudo-first order rate constants for the various physical mixtures of molecular sieves are shown as squares. The measured pseudo-first order rate constants roughly correspond to the values predicted by a simple weighted average of the catalyst activities, as shown by the dashed line.

The prime olefin selectivity of the mixtures shows noticeably different behavior. The predicted selectivity based on a weighted average of the molecular sieves is indicated by the dotted line. As shown by the diamond symbols, the measured selectivity of the mixtures is noticeably greater than the selectivity predicted by a weighted average. For example, for the mixture having a ratio of intergrowth material to SAPO-34 type molecular sieve of 0.25:0.75, the measured prime olefin selectivity has dropped only from about 74.5% to about 74%. By contrast, the prediction based on a weighted average of the catalysts is less than 73%.

FIG. 1 shows that the influence of the SAPO-34 type molecular sieve on the prime olefin selectivity is lower than would be expected based on the relative proportions of the molecular sieves. Based on FIG. 1, the apparent amount of SAPO-34 type molecular sieve in the physical mixture is only about ⅓ or less of the actual amount in the mixture. In terms of the modified weighted average formula (2) as described above, $$\beta * x * P_A + (1\beta * x) * P_B = P_{mix}$$

the value of β when determining the selectivity of mixture of the SAPO-34 type molecular sieve and the intergrowth material should be 0.33 or less.

Figure 2:
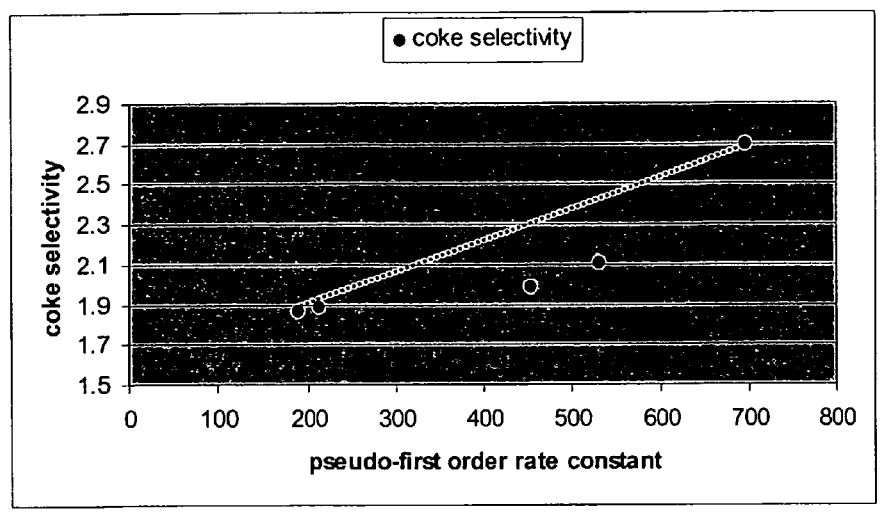
FIG. 2 depicts the coke selectivity for a series of catalyst mixtures according to an embodiment of the invention.

FIG. 2 shows the coke selectivity for the mixture. The bottom axis in FIG. 2 corresponds to the calculated activities (pseudo-first order rate constants) of the mixtures shown in FIG. 1. The vertical axis shows the percentage of coke formed during the conversion reactions. The data points correspond to the measured coke selectivities for each molecular sieve or molecular sieve mixture. The line indicates the predicted coke selectivity based on a weighted average of the coke selectivity for each molecular sieve in a catalyst mixture. As shown by the data points in FIG. 2, the coke selectivity of the mixtures does not linearly increase with increasing weight content of the SAPO-34 type molecular sieve. Instead, the mixtures lead to lower coke production than would be expected based on a weighted average of the individual molecular sieves. Note that the activities of the mixtures roughly correspond to a weighted average of the individual molecular sieves, so the use of the activities as the bottom axis in FIG. 2 is roughly equivalent to displaying the data relative to the catalyst compositions.

Having now fully described this invention, it will be appreciated by those skilled in the art that the invention can be performed within a wide range of parameters within what is claimed, without departing from the spirit and scope of the invention.

We claim:

1. A method for converting an oxygenate feedstock to olefin, comprising:
    contacting a physical mixture of molecular sieves with an oxygenate feedstock, the mixture comprising:
        a first molecular sieve having an activity $K_A$ and a selectivity $S_A$; and
        a second molecular sieve having an activity $K_B$ and a selectivity $S_B$,
    wherein $K_A/K_B$ is at least 1.5, $S_A/S_B$ is less than 1, and the molecular sieves are individually selected from the group consisting of silicoaluminophosphate molecular sieves, silicoaluminate molecular sieves, and metalloaluminophosphate molecular sieves, and
    wherein at least one of the molecular sieves is a silicoaluminophosphate molecular sieve selected from the group consisting of SAPO-34 and SAPO-18.

2. The method of claim 1, wherein $K_A/K_B$ is at least 2.5.

3. The method of claim 1, wherein $K_A/K_B$ is at least 3.5.

4. The method of claim 1, wherein at least one molecular sieve is in the form of a formulated catalyst particle.

5. The method of claim 1, wherein another of the molecular sieves is selected from the group consisting of an intergrowth material, a SAPO-34 molecular sieve, and a SAPO-18 molecular sieve, provided that the physical mixture contains at least two different types of molecular sieves.

6. The method of claim 1, wherein the first molecular sieve has a weight fraction x relative to a total weight of molecular sieve in the mixture, wherein the second molecular sieve has a weight fraction (1−x) relative to the total weight of molecular sieve in the mixture, and wherein an activity of the catalyst mixture $K_{mix}$ satisfies the relation $K_{mix} > 0.9 * [x * K_A + (1-x) * K_B]$.

7. The method of claim 1, wherein the first molecular sieve has a weight fraction x relative to a total weight of molecular sieve in the mixture, wherein the second molecular sieve has a weight fraction (1−x) relative to the total weight of molecular sieve in the mixture, and wherein a prime olefin selectivity $S_{mix}$ of the physical mixture satisfies the relation $S_{mix} = \beta * S_A + (1\beta * x) * S_B$, where β has a value of from 0 to 0.75.

8. The method of claim 1, wherein selectivities $S_A$ and $S_B$ are prime olefin selectivities.

9. The method of claim 1, wherein selectivities $S_A$ and $S_B$ are ethylene selectivities.

10. The method of claim 1, wherein selectivities $S_A$ and $S_B$ are propylene selectivities.

11. The method of claim 1, wherein the first molecular sieve has a weight fraction x relative to a total weight of molecular sieve in the mixture, wherein the second molecular sieve has a weight fraction (1−x) relative to the total weight of molecular sieve in the mixture, and wherein the coke selectivity of the mixture $C_{mix}$ satisfies the relation $C_{mix} < x * C_A + (1-x) * C_B$.

* * * * *